United States Patent
Chen (10) Patent No.: US 7,676,870 B2
(45) Date of Patent: Mar. 16, 2010

(54) PILLOW TO PREVENT SNORING

(75) Inventor: Fu-Ching Chen, 5F., No. 48, Shengli 5th St., Tanzih Township, Taichung County (TW)

(73) Assignees: Fu-Ching Chen, Tanzih Township, Taichung County (TW); Hong Jian Technology Co., Ltd., Tanzih Township, Taichung County (TW)

( * ) Notice: Subject to any disclaimer, the term of this patent is extended or adjusted under 35 U.S.C. 154(b) by 0 days.

(21) Appl. No.: 12/120,957

(22) Filed: May 15, 2008

(65) Prior Publication Data
US 2009/0089932 A1    Apr. 9, 2009

(30) Foreign Application Priority Data

| Oct. 8, 2007 | (TW) | ............................. 96216795 U |
| Nov. 30, 2007 | (TW) | ............................. 96220281 U |
| Nov. 30, 2007 | (TW) | ............................. 96220283 U |

(51) Int. Cl.
*A47G 9/10* (2006.01)

(52) U.S. Cl. .............................................. 5/640; 5/643

(58) Field of Classification Search ..................... 5/636, 5/640, 643, 915
See application file for complete search history.

(56) References Cited

U.S. PATENT DOCUMENTS

| 4,941,478 | A | * | 7/1990 | Takeuchi et al. | ............ 128/848 |
| 6,236,621 | B1 | * | 5/2001 | Schettino | ..................... 368/10 |
| 7,484,255 | B2 | * | 2/2009 | Ho | ................................ 5/636 |

* cited by examiner

*Primary Examiner*—Fredrick Conley
(74) *Attorney, Agent, or Firm*—Egbert Law Offices PLLC (57) ABSTRACT

The present invention provides a pillow to prevent snoring. The pillow includes a base and a mobile seat A shift control assembly shifts the mobile seat between positions and includes a motor, gear set and drive assembly. The shift control assembly also contains a motor output control module for controlling the rotational cycle of output end of the motor. The mobile seat shifts to different positions prior to and after shift based on the set value of the rotational cycle, and this rotational cycle is accurately controlled. The head position or posture happens through different positioning of the mobile seat prior to and after shift, thus helping to stop the snore with improved applicability.

9 Claims, 10 Drawing Sheets

PILLOW TO PREVENT SNORING

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates generally to a pillow to prevent snoring in a sleeper, and more particularly to an innovative pillow that senses a snore and automatically swings the head of the sleeper for the purpose of changing the posture of the sleeper and stopping the snore.

2. Description of Related Art Including Information Disclosed Under 37 CFR 1.97 and 37 CFR 1.98.

An anti-snore pillow has been developed for addressing a noisy sleeper who snores. The principle of this pillow is that an audio sensor senses the snore sound and automatically drives a moving mechanism to the shift of pillow (e.g. swinging horizontally or vertically), thus achieving movement of the head of the sleeper, changing posture and stopping the snoring.

However, the following shortcomings are observed during actual applications.

When the motor of a typical anti-snore pillow is activated to drive the moving mechanism, the stopping position of the moving mechanism cannot be controlled accurately. The location of the moving mechanism prior to and after shifting may remain unchanged. In such case, the head of user will be returned to the original position, without yielding the desired effect for stopping the snore. Notwithstanding the possible difference of stopping and starting positions of a moving mechanism, the prior art anti-snore pillow makes it difficult to achieve the result of its own intended function.

The frequency of the moving mechanism is fixed when the motor of a typical anti-snore pillow is activated to drive the moving mechanism. Due to the snoring frequency specific to every user, the user may be awakened due to excessive swinging operations of anti-snore pillow. Alternatively, the snore is not stopped due to lack of swinging operations, leading to poor efficacy of the prior art anti-snore pillow.

Thus, to overcome the aforementioned problems of the prior art, it would be an advancement in the art to provide an improved structure that can significantly improve efficacy.

Therefore, the inventor has provided the present invention of practicability after deliberate design and evaluation based on years of experience in the production, development and design of related products.

BRIEF SUMMARY OF THE INVENTION

The pillow to prevent snoring of the present invention includes a base, formed by a plate of predefined length, width and thickness, a mobile seat, assembled onto the base in a vertical or lateral shifting, and a shift control assembly, used to control the shift state of the mobile seat. The shift control assembly includes a motor, gear set, and drive assembly. The drive assembly is arranged between the drive portion of the gear set and the mobile seat. The drive assembly includes a circular block with an eccentric hole, a column on the mobile seat, and a coupling plate. When the drive portion rotates, the circular block will be driven for tilting rotation, thus driving the coupling plate to generate a reciprocating shift along with the mobile seat. A motor output control module controls the rotational cycle of the motor, and a snore detector is used to detect the snore of the user. An ECU directs the operation of the shift control assembly based on the sensing signal of snore detector. An upper pad is assembled externally onto the base and mobile seat with a slot for insertion of the snore detector for proper limitation.

DETAILED DESCRIPTION OF THE INVENTION

The features and the advantages of the present invention will be more readily understood upon a thoughtful deliberation of the following detailed description of a preferred embodiment of the present invention with reference to the accompanying drawings.

Figure 1:
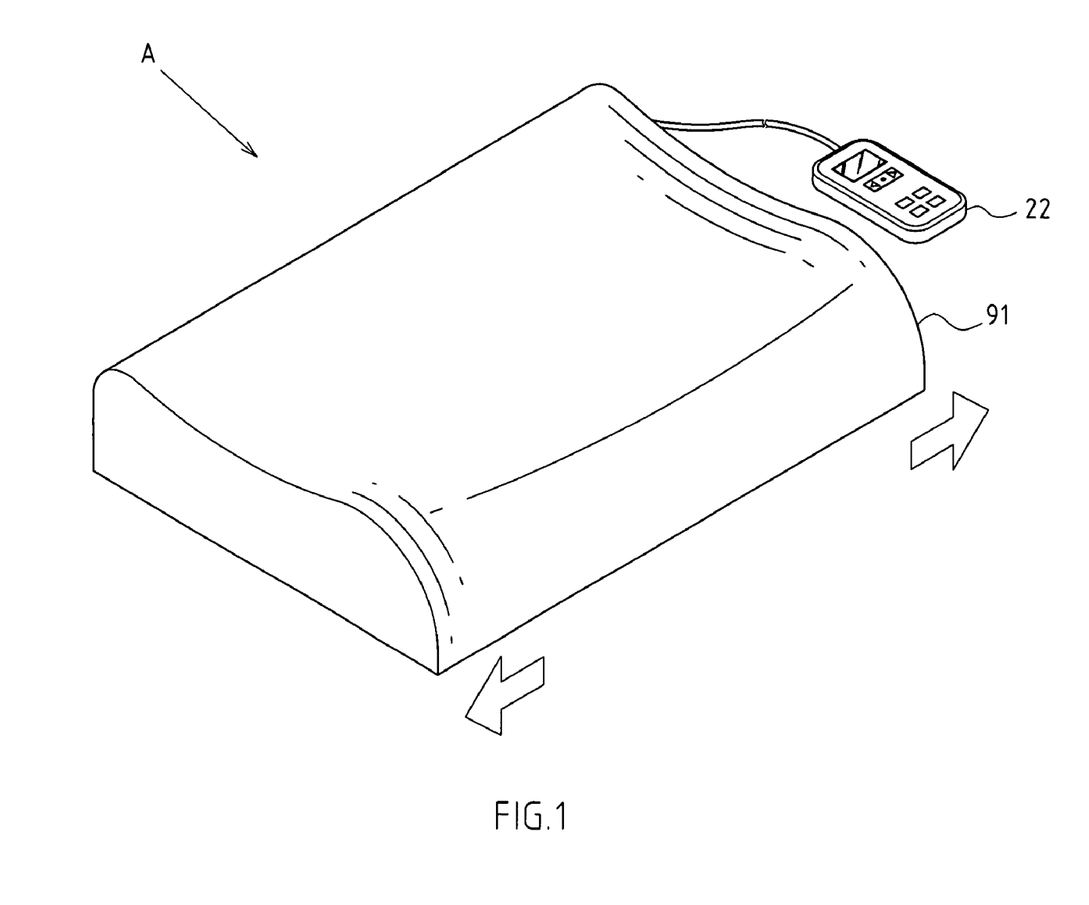
FIG. 1 depicts a perspective view of the pillow to prevent snoring or anti-snore pillow of the present invention.
Figure 2:
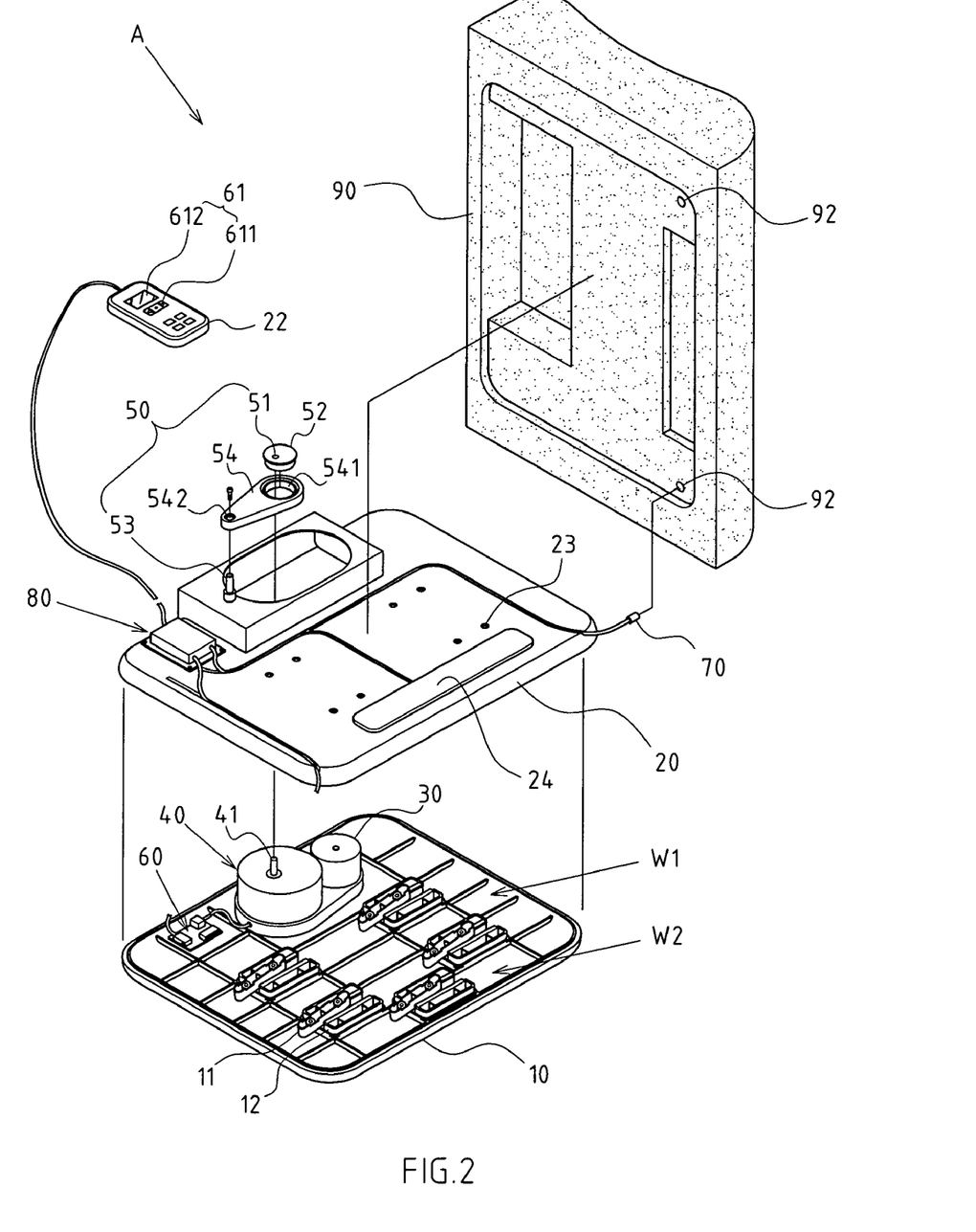
FIG. 2 depicts an exploded perspective view of the anti-snore pillow of the present invention.
Figure 3:
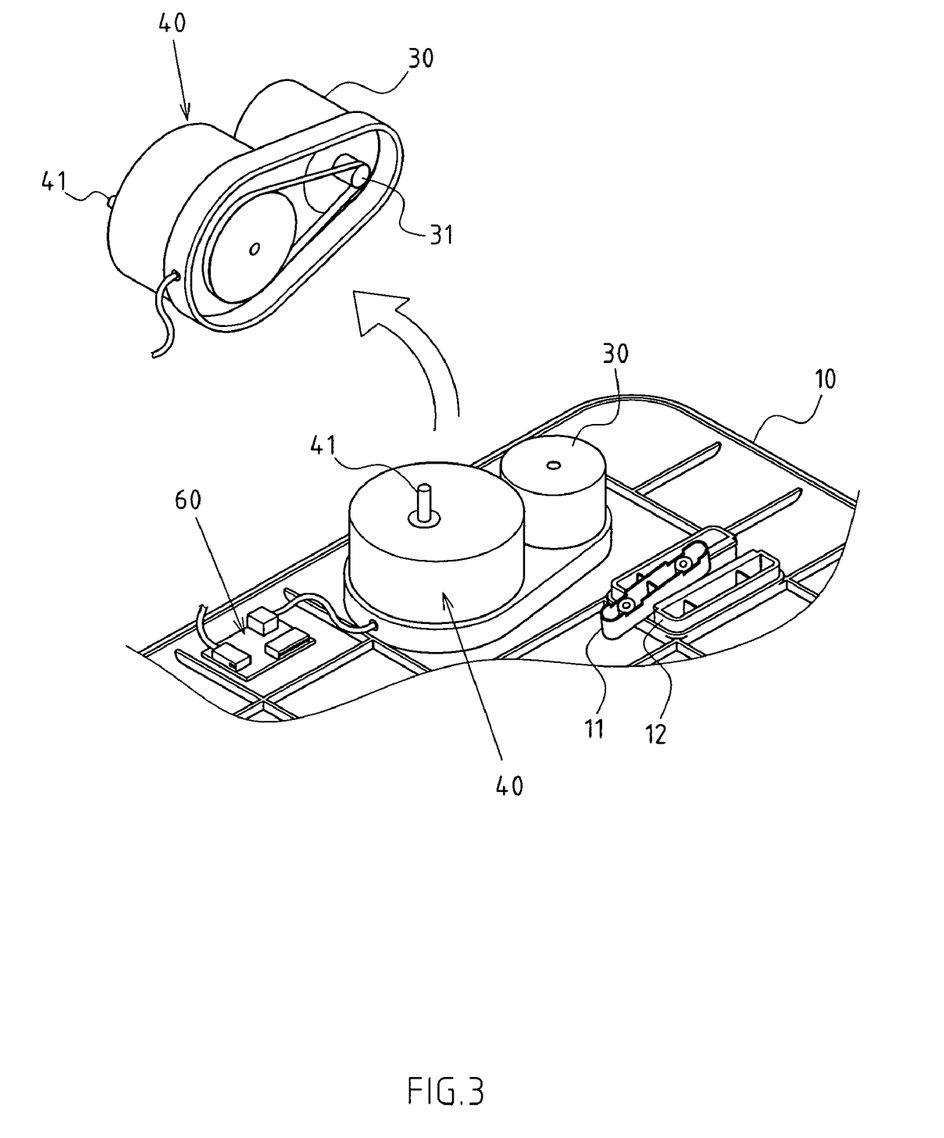
FIG. 3 depicts a partially perspective view of the anti-snore pillow of the present invention.

FIGS. 1-3 depict a preferred embodiment of improved structure of a pillow to prevent snoring of the present invention. The embodiments are provided only for explanatory purposes with respect to the patent claims.

The anti-snore pillow comprises a base 10, which is formed by a plate of predefined length, width and thickness.

A mobile seat 20 is assembled onto the base 10 in a horizontally or vertically shifted or non-shifted state.

A shift control assembly is used to control the state of shift of the mobile seat 20. The shift control assembly comprises a motor 30 or servo motor, gear set 40 and drive assembly 50. The drive assembly 50 is arranged between the drive portion 41 of the gear set 40 and the mobile seat 20. The drive assembly 50 of the present invention comprises a circular block 52 with an eccentric hole 51, a column 53 on the mobile seat 20, and a coupling plate 54. The eccentric hole 51 of the circular block 52 is sleeved onto the drive portion 41 of the gear set 40. The coupling plate 54 is a long plate, having one end provided with the first connecting hole 541 for coupling with the circular block 52 and another end provided with the second connecting hole 542 for coupling with the column 53 of the mobile seat 20. When the drive portion 41 of the gear set 40 is rotated, the circular block 52 will be driven for tilting rotation, thus driving the coupling plate 54 to generate a reciprocating shift along with the mobile seat 20.

A motor output control module 60 controls the rotational cycle of output axle 31 of the motor 30.

A snore detector 70 detects the snore of the user.

An ECU 80 directs the operation of the shift control assembly based on the sensing signal of snore detector 70.

An upper pad 90 is assembled externally onto the base 10 and mobile seat 20. The upper pad 90 is made of soft and flexible materials (e.g. sponge or other foam material). A cloth cover 91 is coated onto the upper pad 90, and a slot 92 is placed at bottom of the upper pad 90, shown in FIG. 2, to insert the snore detector 70 for proper limitation of the snore detector 70.

The mobile seat 20 is provided with a pressing power starter 21, which is connected to ECU 80, so as to turn on the power necessary for ECU 80, motor 30 and snore detector 70 when the power starter 21 is pressed.

Figure 4:
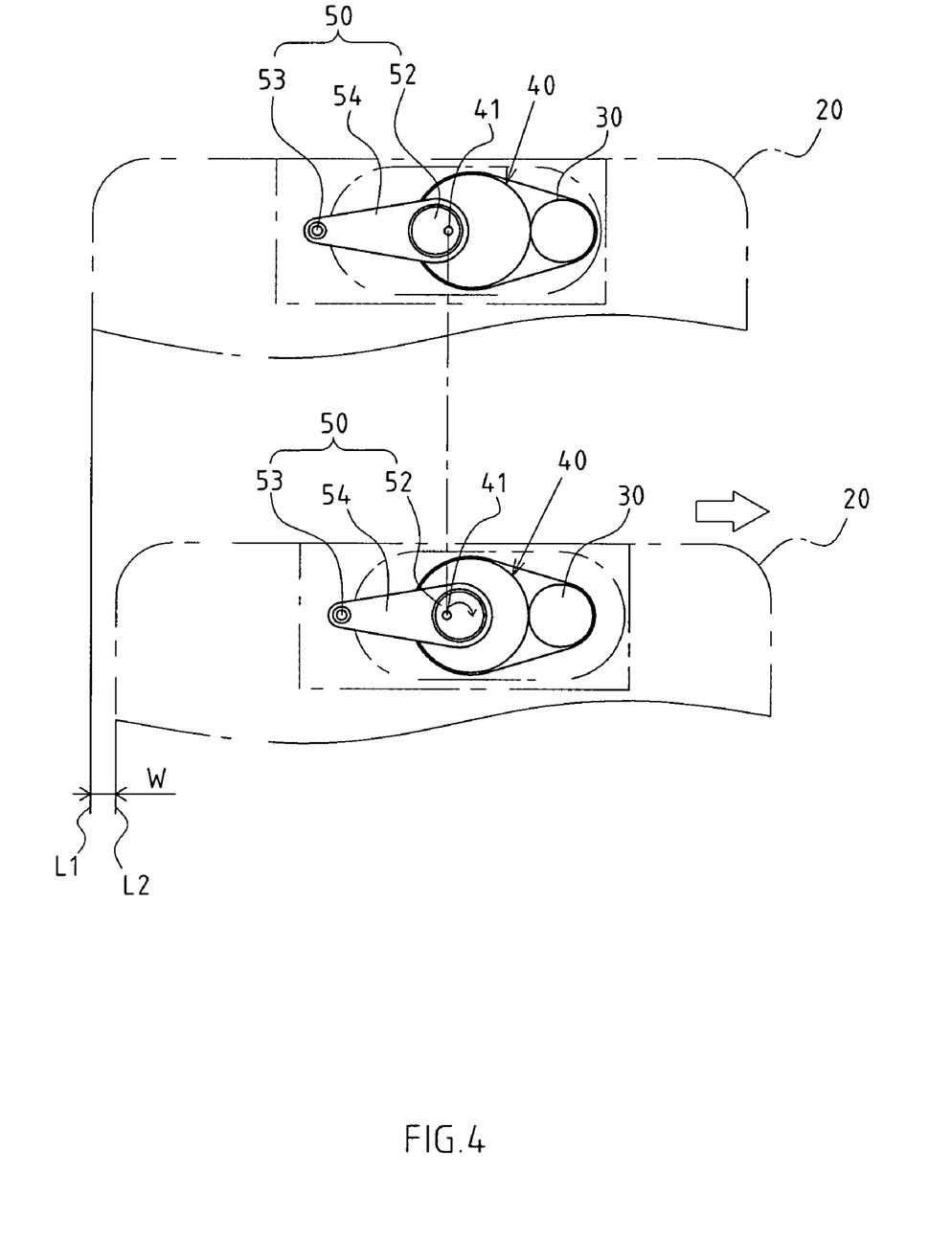
FIG. 4 depicts a schematic view of the anti-snore pillow of the present invention showing the position difference of mobile seat prior to and after shift.
Figure 5:
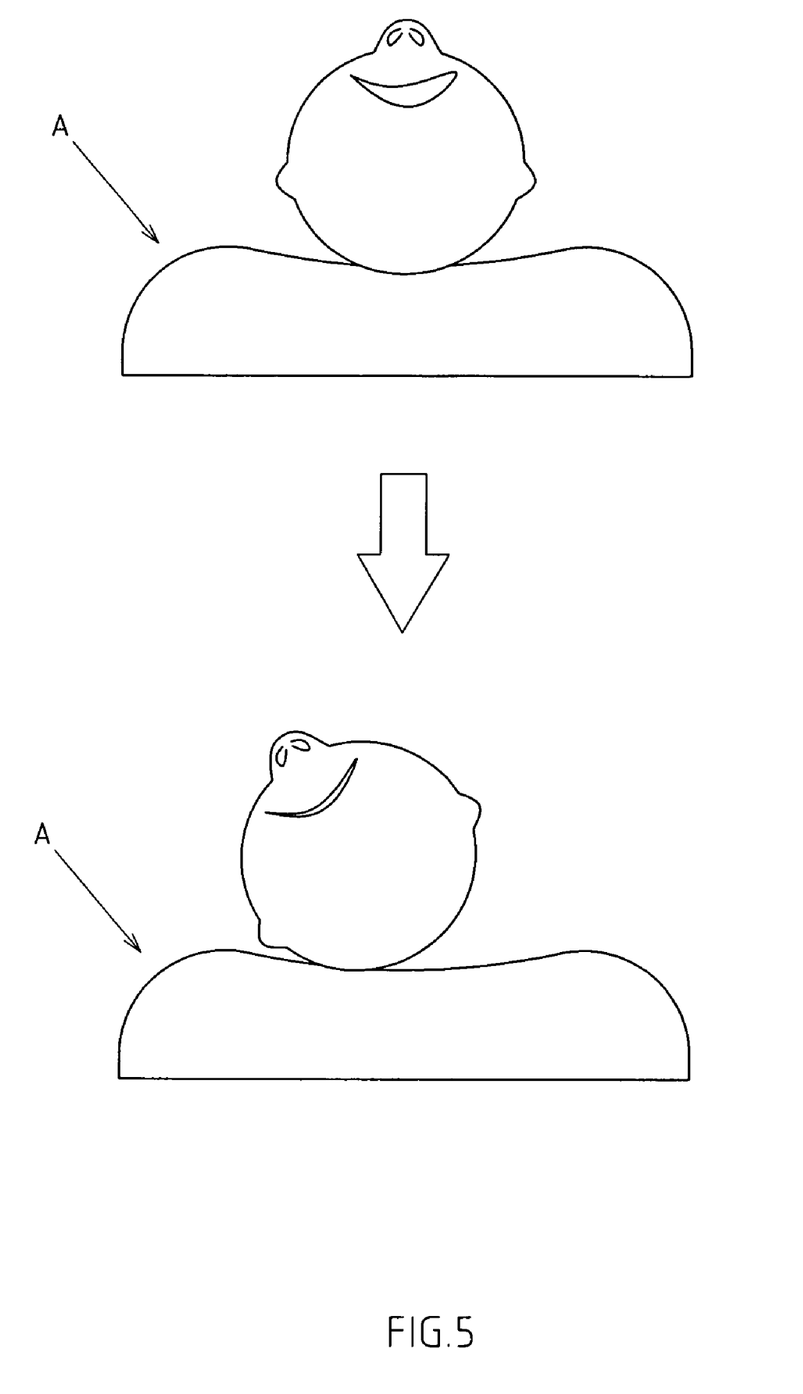
FIG. 5 depicts a schematic view of the anti-snore pillow of the present invention that can change the head position and posture of the user.

The motor output control module 60 controls the set value of rotational cycle of output axle 31 of the motor 30, enabling the mobile seat 20 to be located at different positions prior to and after shift. Specifically, the existing servo motor technology can be used to control accurately the positioning point through a controller. It is assumed that, after 100 cycles of rotation by the output end 31 of the motor 30, the mobile seat is allowed to generate a predefined reciprocating shift (i.e. return to original point) through variable drive of gear set 40, then the motor output control module 60 sets the rotation number of output end 31 of the motor 30 as 50 cycles. The setting state is shown in FIG. 4, the position of the mobile seat 20 prior to shift is at the leftmost site of maximum shift stroke (marked by L1), and the position after shift is at a rightmost site of maximum shift stroke (marked by L2), thus generating a position difference W whenever the mobile seat 20 is activated (alternation of left and right positions). Similarly, different positioning states could be generated from the aforementioned principle, for example, the mobile seat 20 could be positioned at leftmost or rightmost or any other optional sites. With the aforementioned structures, the anti-snore pillow A can be operated as shown in the upper diagram of FIG. 5. It is assumed that the position of the head is kept upward prior to shift of the anti-snore pillow A, the position of the head will be changed obliquely due to the position change after shift of anti-snore pillow A (shown in lower diagram of FIG. 5), thereby achieving the purpose of stopping the snore.

Figure 6:
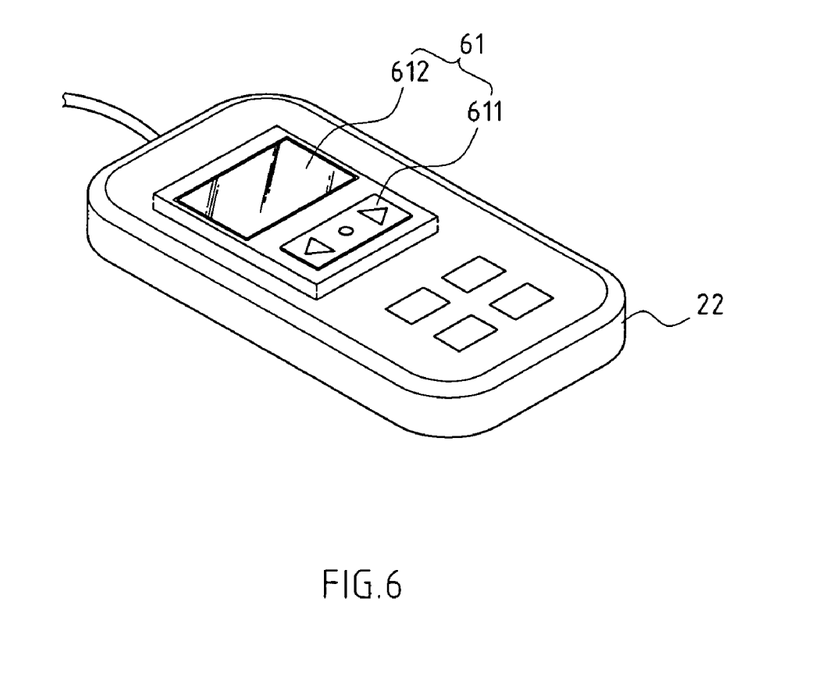
FIG. 6 depicts a perspective view of the application of the manual regulating module of the present invention.
Figure 7:
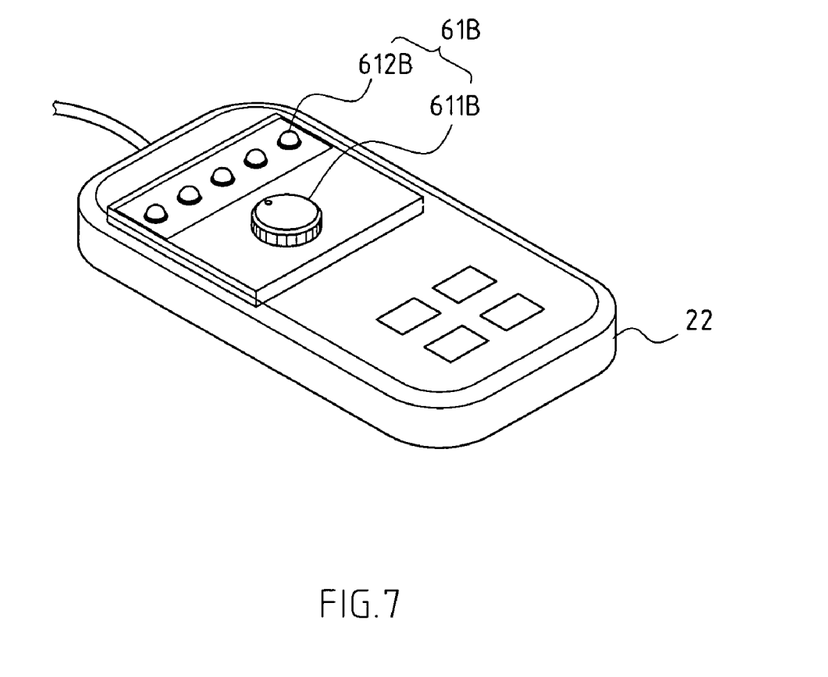
FIG. 7 depicts another perspective view of the application of the manual regulating module of the present invention.

Alternatively, as the motor output control module 60 controls the rotational cycle of output axle 31 of the motor 30, it is possible to control the shift frequency of the mobile seat in conjunction with a regulating module. The regulating module 61 is used to regulate the actuating frequency of motor 30 and the mobile seat 20. The actuating frequency of mobile seat 20 is regulated by changing the rotational cycle of output axle 31 of the motor 30. The regulating module 61 is of a manual type, with the preferred embodiments shown in FIGS. 2, 6. The regulating module 61 can be assembled onto a controller 22 protruded from the mobile seat 20 and arranged in parallel with other functional keys of the anti-snore pillow A. The regulating module 61 is provided with a regulating component 611 and a display portion 612. The regulating component 611 is a push-button type as shown in FIG. 6, or, the regulating component 611B of the regulating module 61B is a rotary knob as shown in FIG. 7, or a toggle type. The display portion 612 is an LCD as shown in FIG. 6, or the display portion 612B of the regulating module 61B is a lamp LED as shown in FIG. 7, wherein the lamps of different colors represent the operating frequencies such as: 3, 5, 7, 9.

Figure 8:
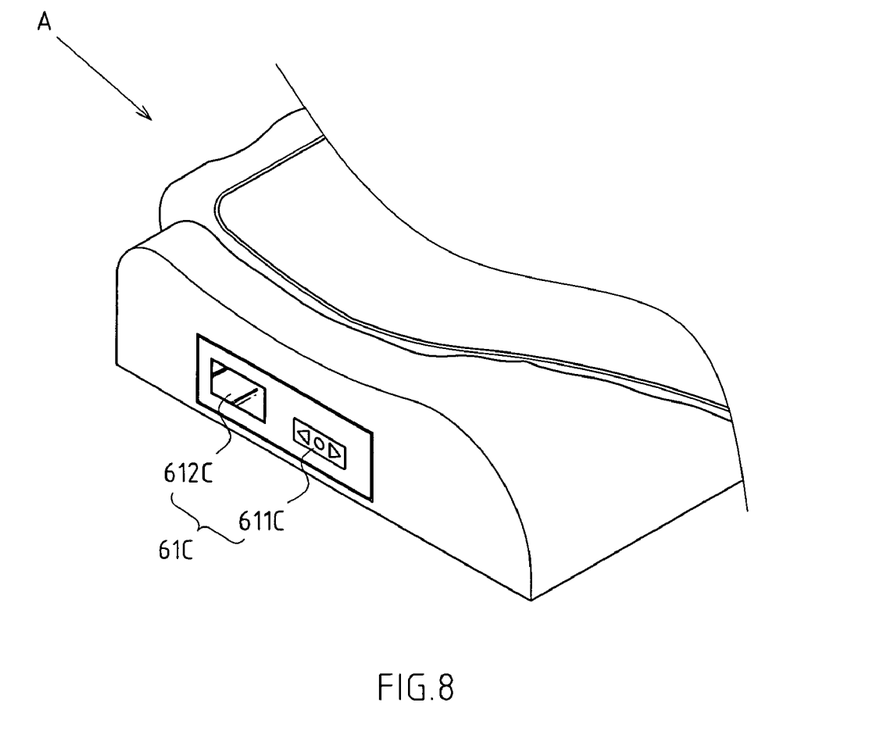
FIG. 8 depicts a perspective view of a position change of the regulating module of the present invention.

Referring to FIG. 8, the regulating module 61C, along with the regulating component 611C and display portion 612C is laterally arranged onto the anti-snore pillow A.

Figure 9:
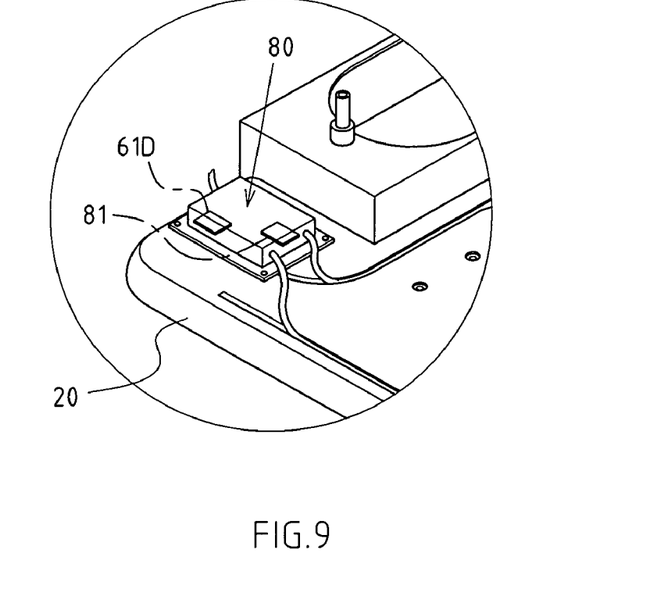
FIG. 9 depicts a perspective view of application of the auto regulating module of the present invention.
Figure 10:
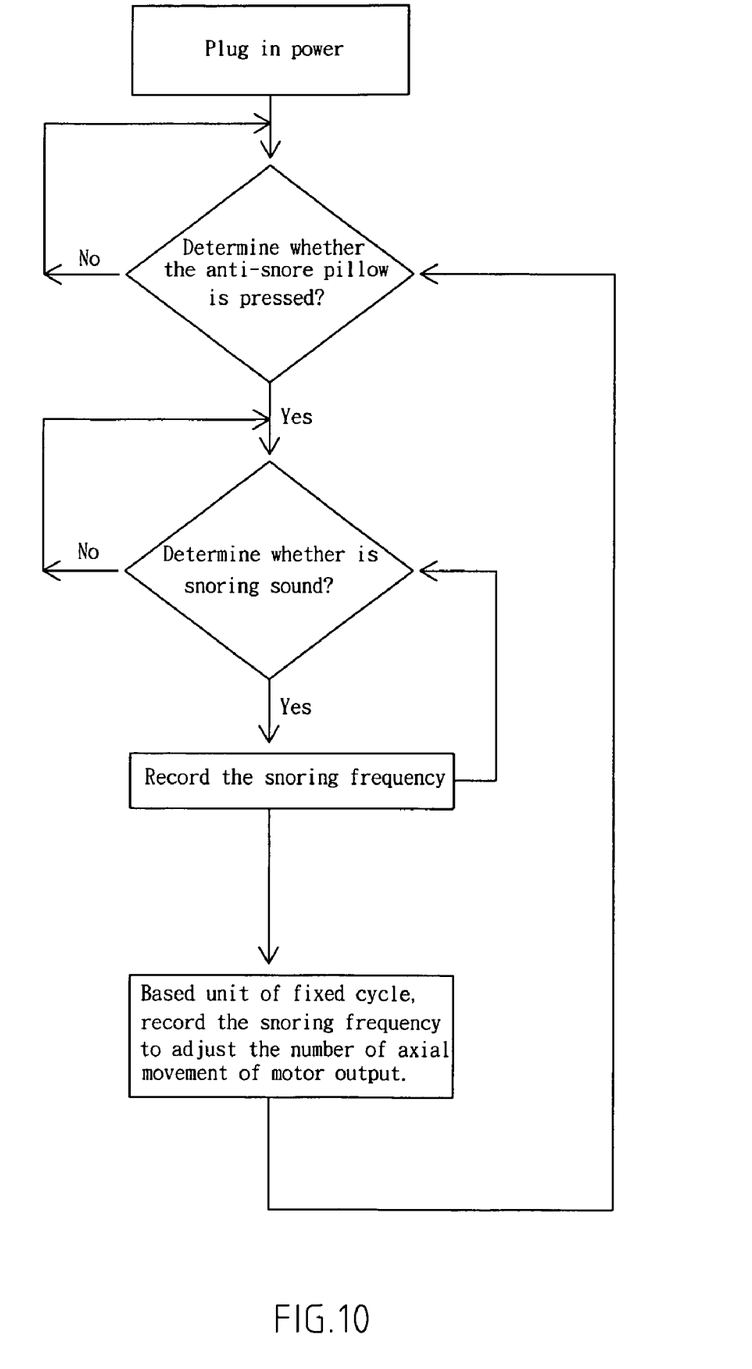
FIG. 10 depicts a block diagram illustration of the operating process of auto regulating module of the present invention.

Referring also to FIG. 9, the regulating module 61D is an auto-regulating type. The regulating module 61D is electrically connected to ECU 50. An actuating frequency detector module 81 is electrically connected to ECU 80 and regulating module 60D. The actuating frequency detector module 81 records the actuating frequency sensed by the snore detector 70 of the anti-snore pillow A (shown in FIG. 2). The regulating module 61D makes statistics of the snoring frequency through a preset cycle (e.g. every 1 h), and automatically regulates the actuating frequency of the output axle 31 of motor 30. For instance, the internal parameter value of ECU 80 is set as 5 snores detected within 1 h. As such, when the actuating frequency detector module 81 detects over 5 snores within 1 h, the regulating module 61D will increase automatically the actuating frequency of output axle 31 of the motor 30 in the next stroke. Conversely, when the actuating frequency detector module 81 detects smaller snores (less than 5) within 1 h, the regulating module 61D will reduce automatically the actuating frequency of output axle 31 of the motor 30 in the next stroke, thereby adjusting flexibly the shift state of anti-snore pillow A to achieve the optimal effect. The operating process of anti-snore pillow of the present invention is described normatively by a block diagram as shown in FIG. 10. When the anti-snore pillow is switched on, it is possible to judge if the pillow has been pressed and if there is snore, then, the regulating module makes statistics of the snoring frequency through a preset cycle and automatically regulates the actuating frequency of the output axle of motor. Additionally, both manual and auto regulating modules 61, 61D can be implemented on the anti-snore pillow, allowing to switch manual and auto operations through a switching mechanism.

Figure 11:
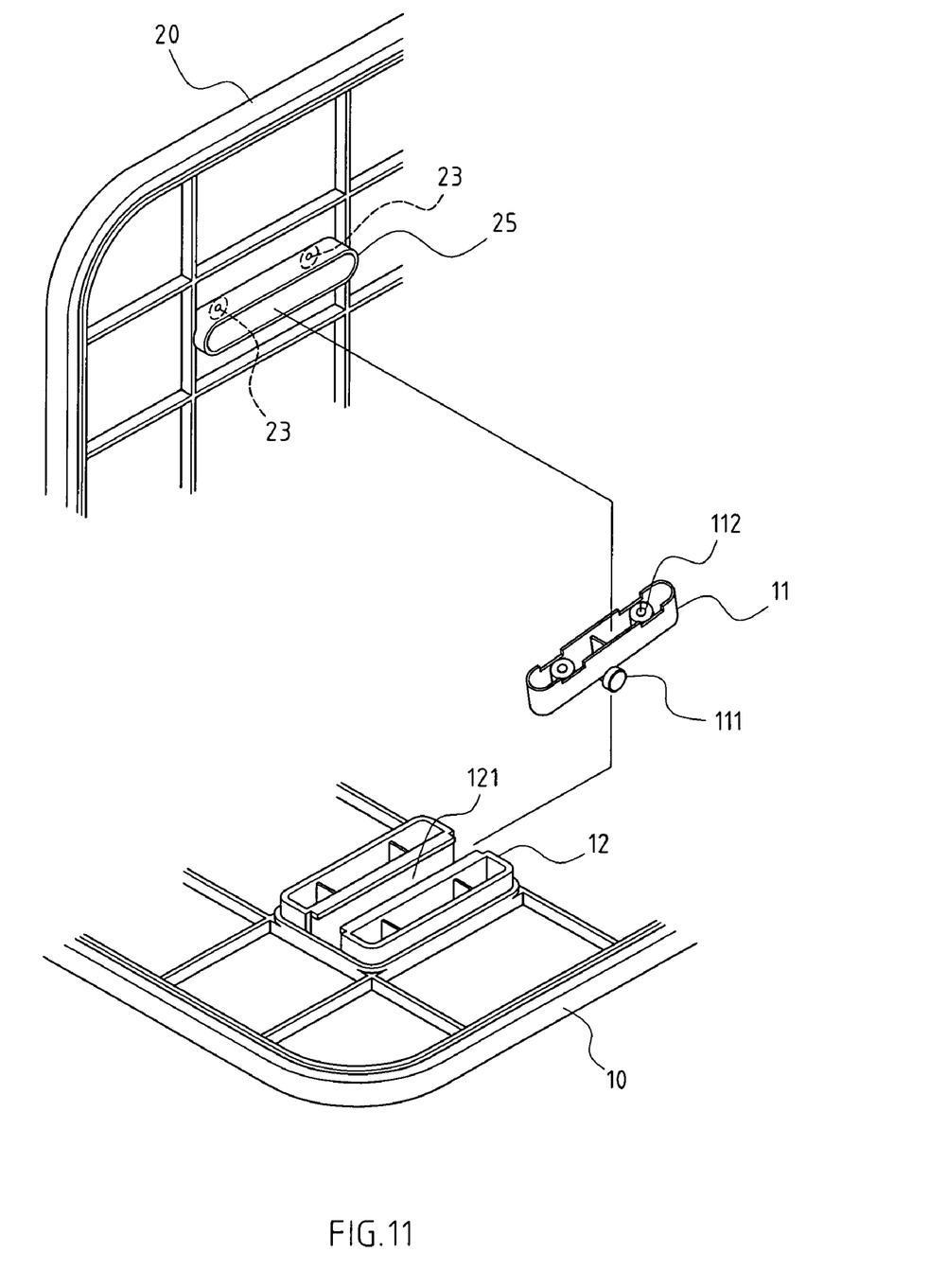
FIG. 11 depicts an exploded perspective view of the slide and guide rail of the present invention.

Referring to FIGS. 2, and 11, a plurality of slides 11 and guide rails 12 are alternatively arranged between the mobile seat 20 and base 10 correspondingly to the resting area of head and neck (marked by W1 in FIG. 2). The relative motion direction of the slides 11 and guide rails 12 is the same as the transverse shift direction of the mobile seat 20.

Referring also to FIG. 2, at least a group of slides 11 and guide rails 12 are arranged between the mobile seat 20 and base 10 corresponding to the resting area of the neck (marked by W2 in FIG. 2). The relative motion direction of the slides 11 and guide rails 12 is the same as the transverse shift direction of the mobile seat 20. As the neck of the user will be subject to bigger pressure when the head is rested on the anti-snore pillow, the mobile seat 20 will shift more reliably with slide 11 and guide rail 12.

Figure 12:
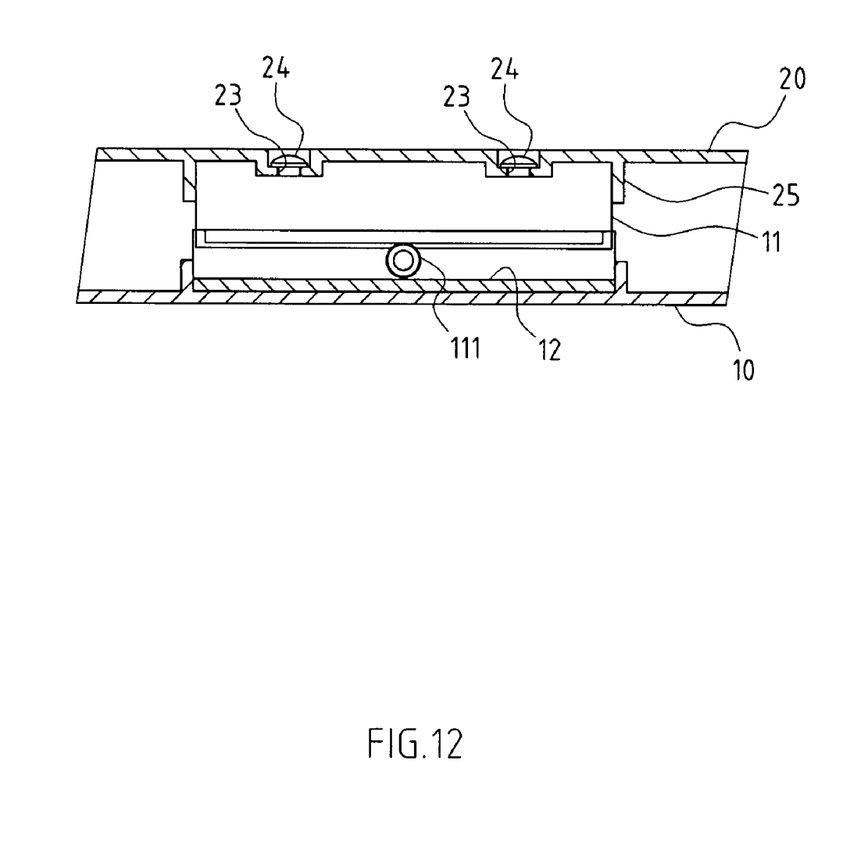
FIG. 12 depicts a sectional view of the slide and guide rail of the present invention.
Figure 13:
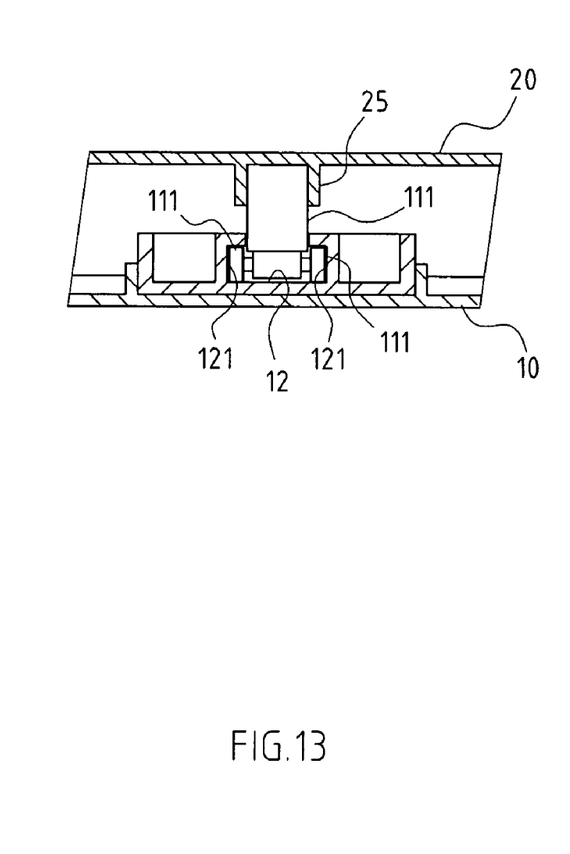
FIG. 13 depicts another sectional view of the slide and guide rail of the present invention.

Referring to FIGS. 11, 12, and 13, the slide 11 is a long base. A roller set 111 protrudes from both sides of the slide 11, being placed centrally onto the bottom of the slide 11. Screwing holes 112 are arranged on top of the slide 11. The mobile seat 20 is provided with through-holes 23 for assembly of the slide 11, which are aligned with the screwing holes 112, thus allowing for screwing and positioning the slide 80 via bolts 24. The cross-section of the guide rail 12 is shown in FIG. 13, wherein two lateral troughs 121 are defined for embedding two roller sets 111 of the slide 11. Moreover, at the bottom of the mobile seat 20 for assembly of the slide 11, a frame 25 is provided for embedding the top of the slide 11.

In the case of reciprocating shift of the mobile seat 20, the relative motion of slide 11 and guide rail 12 is shown in FIGS. 12, and 13. The roller sets 111 at both sides of the slide 11 will roll reciprocated in the lateral trough 121 of the guide rail 12, thus yielding a rolling support for the mobile seat 20.

Based upon this innovative invention with a motor output control module, it is possible to control accurately the rotational cycle of the motor, and change the head posture through different positioning of the mobile seat prior to and after shifting, thus helping to stop the snore with improved applicability.

Based upon this innovative invention with a regulating module, the shift and actuating frequency of the anti-snore pillow will be regulated flexibly to meet the users' demands. The anti-snore pillow could be brought into full play for achieving better applicability and meeting diversified demands.

Based upon this innovative invention, a plurality of slides and guide rails are alternatively arranged between the mobile seat and base corresponding to the resting area of the head and neck, respectively. The slides and guide rails are mated with the resting area of the head and neck during transverse shift of the mobile seat, so the head of the user could be supported more stably, ensuring more smooth operation of the mobile seat, avoiding efficiently the noise and improving greatly the performance of the anti-snore pillow.

Based on the structures, at least a group of slides and guide rails are arranged between the mobile seat and base corresponding to the resting area of neck. The neck of the user will be subject to bigger pressure when the head is rested on the anti-snore pillow, the mobile seat will shift more reliably with slide and guide rail, thus further improving the performance and applicability of the anti-snore pillow.

Although the invention has been explained in relation to its preferred embodiment, it is to be understood that many other possible modifications and variations can be made without departing from the spirit and scope of the invention as hereinafter claimed.

I claim:

1. An anti-snore pillow apparatus comprising:
    a base;
    a mobile seat shiftably mounted onto said base;
    a shift control means for controlling a shifting of said mobile seat with respect to said base, said shift control means comprising a motor and a gear set and a drive assembly, said motor having an axle extending downwardly therefrom, said gear set having a sheave positioned at a bottom thereof and a shaft extending from a top thereof, said axle of said motor having a belt engaged therewith and received in said sheave of said gear set, said drive assembly connected to said shaft of said gear set and cooperative with said mobile seat so as to controllably shift a position of said mobile seat;
    a mobile output control means affixed to said base and operatively connected to said motor for controlling a rotational cycle of said axle of said motor;
    a snore detecting means for detecting a snore of a person;
    a processing means connected to said snore detecting means and to said mobile output control means, and processing means for directing an operation of said shift control means based on the detecting of the snore; and
    an upper pad mounted over said base and said mobile seat.

2. The anti-snore pillow apparatus of claim 1, said mobile output control means for controlling the rotational cycle of said axle of said motor so as to move said mobile seat from a first position to a second position relative to the detected snore.

3. The anti-snore pillow apparatus of claim 2, said first position being a leftmost position, said second position being a rightmost position.

4. The anti-snore pillow apparatus of claim 1, said mobile output control means for controlling a frequency of shift of said mobile seat.

5. The anti-snore pillow apparatus of claim 1, said drive assembly comprising a circular block having an eccentric hole and a coupling plate, said mobile seat having a column, said eccentric hole being sleeved onto said shaft of said gear set, said coupling plate having a first connecting hole at one end thereof connected to said circular block, said coupling plate having a second connecting hole at an opposite end thereof connected to said column of said mobile seat.

6. The anti-snore pillow apparatus of claim 1, said motor output control means comprising a regulating module having a regulating component and a display, and a regulating module being electrically connected to said processing means, the apparatus further comprising:
    an actuating frequency detecting means electrically connected to said processing means and to said regulating module, said actuating frequency detecting means for recording an actuating frequency detected by said snore detecting means.

7. The anti-snore pillow apparatus of claim 1, said mobile seat having a pressing power starter, said power starter connected to said processing means so as to provide power to said processing means and said motor and said snore detecting means.

8. The anti-snore pillow apparatus of claim 1, further comprising:
    a plurality of slides and guide rails alternatively arranged between said mobile seat and said base in an area corresponding to a head resting area of a person using the pillow, said plurality of slides and guide rails movable and aligned with a shift direction of said mobile seat.

9. The anti-snore pillow apparatus of claim 8, said slide having an elongated base, said slide having a roller set protruding from opposite sides thereof, said slide having screwing holes at a top thereof, said mobile seat having through holes therein and aligned with said screwing holes, said slide having a bolt extending through the screwing hole and the through hole.

* * * * *